US012601702B2

(12) United States Patent (10) Patent No.: US 12,601,702 B2
Cui (45) Date of Patent: Apr. 14, 2026

(54) METHANE SENSOR

(71) Applicant: Peking University, Beijing (CN)

(72) Inventor: Yue Cui, Beijing (CN)

( * ) Notice: Subject to any disclaimer, the term of this patent is extended or adjusted under 35 U.S.C. 154(b) by 0 days.

(21) Appl. No.: 18/395,667

(22) Filed: Dec. 25, 2023

(65) Prior Publication Data

US 2024/0319129 A1 Sep. 26, 2024

(30) Foreign Application Priority Data

Mar. 22, 2023 (CN) .......................... 202310280278.8

(51) Int. Cl.
| | |
|---|---|
| *G01N 27/30* | (2006.01) |
| *G01N 27/404* | (2006.01) |
| *G01N 33/00* | (2006.01) |

(52) U.S. Cl.
CPC ......... *G01N 27/30* (2013.01); *G01N 27/4045* (2013.01); *G01N 33/0047* (2013.01)

(58) Field of Classification Search
CPC . G01N 27/30; G01N 27/4045; G01N 33/0047
See application file for complete search history.

(56) References Cited

U.S. PATENT DOCUMENTS

2012/0181173 A1* 7/2012 Ochoteco Vaquero ......................
G01N 33/54326
204/403.01
2020/0300802 A1 9/2020 Pope et al.

FOREIGN PATENT DOCUMENTS

| CN | 109470752 A | 3/2019 | |
|---|---|---|---|
| CN | 112697864 A | 4/2021 | |
| CN | 114324495 A | 4/2022 | |
| WO | WO 2010054420 A1 * | 5/2010 | ............. G01N 27/12 |

OTHER PUBLICATIONS

IUPAC definition of "copolymer" (and "terpolymer") IUPAC Compendium of Chemical Terminology Copyright © 2014 IUPAC (Year: 2014).*
EPO machine-generated English language translation of WO 2010/054420 A1 (Year: 2010).*
EPO machine-generated English language translation of CN 112697864A (Year: 2021).*

(Continued)

*Primary Examiner* — Alexander S Noguerola

(57) ABSTRACT

A methane sensor includes a substrate, a conductive connection electrode, and a sensing electrode, the conductive connection electrode is arranged on the substrate, and the sensing electrode is covered on the conductive connection electrode, the sensing electrode is a layer of conductive polymer film, and the conductive connection electrode is coated with an insulating layer in addition to the sensing area. The sensing electrode adopts one of poly (3,4-ethylenedioxythiophene):poly (styrene sulfonic acid), polyaniline, polythiophene and polypyrrole, which is made into a film by a screen printing, inkjet printing or other coating method in the form of liquid or paste. The present invention adopts the above methane sensor, with a small and stable sensor, realizing sensitive and rapid detection of methane, and solving the problems of high power consumption of methane sensors in the prior art, high working temperature, expensive and bulky casing of the equipment, and high price.

5 Claims, 9 Drawing Sheets

(56) References Cited

OTHER PUBLICATIONS

Zuquan Wu, et al., Room Temperature Methane Sensor Based on Graphene Nanosheets/Polyaniline Nanocomposite Thin Film, IEEE Sensors Journal, 2013, pp. 777-782, vol. 13 No.2.

Syed Khasim, et al., Design and development of highly sensitive PEDOT-PSS/AuNP hybrid nanocomposite-based sensor towards room temperature detection of greenhouse methane gas at ppb level, RSC Advances, 2021, pp. 15017-15029, vol. 11, Royal Society of Chemistry.

Apsar Pasha, et al., Highly sensitive ethylene glycol-doped PEDOT—PSS organic thin films for LPG sensing, RSC Advances, 2018, pp. 18074-18083, vol. 8, The Royal Society of Chemistry.

\* cited by examiner

METHANE SENSOR

CROSS REFERENCE TO THE RELATED APPLICATIONS

This application is based upon and claims priority to Chinese Patent Application No. 202310280278.8, filed on Mar. 22, 2023, the entire contents of which are incorporated herein by reference.

TECHNICAL FIELD

The present invention relates to the field of methane gas detection technology, in particular to a methane sensor.

BACKGROUND

To achieve the sustainable development of energy and environment, the production and consumption of natural gas have increased rapidly. It is predicted that natural gas will become the second most widely used energy in the future. Methane is the main component of natural gas. As a source of power generation and heating, it is an important factor in global warming and climate change. Compared with coal, methane emissions and production costs are relatively low in the combustion process. There are some safety problems in the application of methane. Methane is colorless and odorless, and its concentration in the air is about 5% to 15%, which is explosive. Due to pipeline aging, corrosion, defects and other factors, natural gas pipeline leakage accidents often occur, and methane leakage may also occur in coal mining operations and petroleum fractionation plants. Methane leakage may threaten people's lives and property safety. In order to quickly and reliably identify methane leakage, the development of intelligent, real-time detection, and high-sensitivity methane sensors is the key to safe application of methane.

There are many kinds of methane sensors in the existing technology, and according to different principles, methane sensors can be divided into optical sensors, capacitive sensors, calorimetric sensors, resonant sensors, acoustic sensors, pyroelectric sensors, semiconductor metal oxide sensors and electrochemical sensors.

However, the existing sensors have some shortcomings, such as high power consumption, high operating temperature, expensive and cumbersome equipment shell, and high price.

SUMMARY

The purpose of the present invention is to provide a methane sensor, which solves the problems of high power consumption, high working temperature, expensive and bulky shell and expensive price of the equipment.

To achieve the above purpose, the present invention provides a methane sensor, including a substrate, a conductive connection electrode and a sensing electrode, wherein the conductive connection electrode is arranged on the substrate, and the sensing electrode is covered on the conductive connection electrode, the sensing electrode is a layer of a conductive polymer film, and the conductive connection electrode is coated with an insulating layer in addition to a sensing area.

Preferably, a conductive polymer is a kind of conductive polymer, which is poly (3,4-ethylenedioxythiophene):poly (styrene sulfonic acid) (PEDOT:PSS), polyaniline, polythiophene and polypyrrole, and the conductive polymer is made into the conductive polymer film by screen printing, printing method, or coating method in a form of liquid or paste.

Further preferably, a conductive polymer is PEDOT:PSS.

Preferably, the conductive connection electrode is made of one material of a gold composite paste, a platinum composite paste and a carbon composite paste, and is manufactured by screen printing or other printing method.

Preferably, a material of the substrate is at least one of terpolymers of flexible materials polyethylene terephthalate, polyimide, polyvinyl chloride, acrylonitrile butadiene, and styrene, or one of hard materials silicon, glass, and ceramics.

Preferably, the conductive connection electrode is an electrochemical electrode, including two electrodes or three electrodes, when there are two electrodes, it is a working electrode and a counter electrode, when there are three electrodes, it is a working electrode, a reference electrode and a counter electrode.

Preferably, a concentration of conductive polymer solution is 1-100%, and a volume is 0.1-10 μL.

Further preferably, a concentration of PEDOT:PSS solution is 100%, and a volume of PEDOT:PSS solution is 0.7 μL.

A preparation method of the methane sensor includes the following steps:

(1) preparation of substrate washing a substrate sheet and cleaning, then cutting it into 1 cm×5 cm uniform small pieces as the substrate;

(2) fabrication of the conductive connection electrode printing or screen printing an electrode material on the substrate with a screen printer or a printer to form a conductive connection electrode 5, and then putting the conductive connection electrode into an oven for drying, using the conductive connection electrode as a wire to connect the sensing electrode, and further connecting a detection instrument or a circuit board through an interface and further connect the detection instrument or the circuit board through the interface;

(3) manufacturing of the insulating layer making an insulating layer on the conductive connection electrode by the screen printer or a printer to expose the sensing area connecting an external interface part and the sensing electrode, and then drying in the oven;

(4) fabrication of the sensing electrode dropping a conductive polymer solution at a junction of the sensing electrode in the sensing area, and drying in the oven to form a film, that is, the sensing electrode, then taking out and storing in a refrigerator.

Preferably, an oven drying temperature range is 30-100° C., a drying time is 5-100 min.

Preferably, a temperature of refrigerator storage is 0-8° C.

The beneficial effects of the present invention are as follows:

(1) preparing a methane sensor by coating an electrically connected electrode, a PEDOT:PSS sensing electrode, and an insulating layer on a flexible substrate, the sensor is small and stable, and realizes sensitive and rapid detection of methane, the volume is small, so that the methane sensor has a smaller shell, which reduces the weight of the sensor and reduces the cost.

(2) using PEDOT:PSS polymer as the sensing electrode, the molecules in the film of PEDOT:PSS solution accumulate in an orderly manner to form a conduction band, the conduction band has a conductive layer and a resistance layer, oxygen in the air is adsorbed on PEDOT:PSS and converted into chemically adsorbed oxygen, in the presence of methane, methane molecules react with chemically adsorbed oxygen to produce $CO_2$, $H_2O_2$ and electrons, therefore, the electrons enter the conduction band, resulting in an increase in the thickness of the conductive layer and a decrease in the thickness of the resistance layer, which reduces the resistance of the PEDOT:PSS, after the PEDOT:PSS is connected to the voltage, the current response will change due to the change of its resistance, therefore, methane can be detected in the air according to the corresponding change current, so that the prepared methane sensor has the characteristics of high flexibility, low cost, fast response and high sensitivity.

The following is a further detailed description of the technical scheme of the present invention through drawings and implementation examples.

TAG OF DIAGRAM

Figure 1:
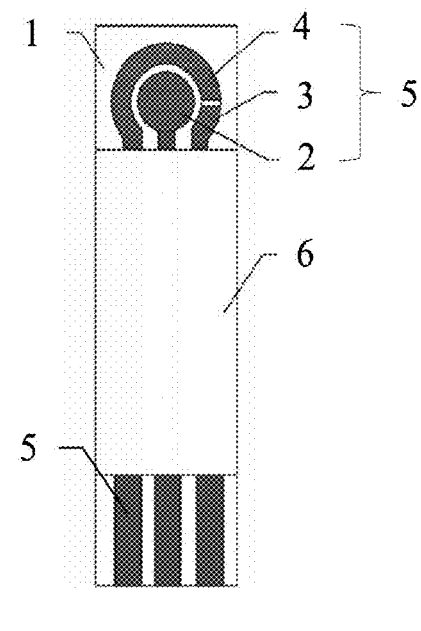
FIG. 1 is a schematic diagram of the methane sensor of the present invention, in which the sensing electrode is not shown.
Figure 2:
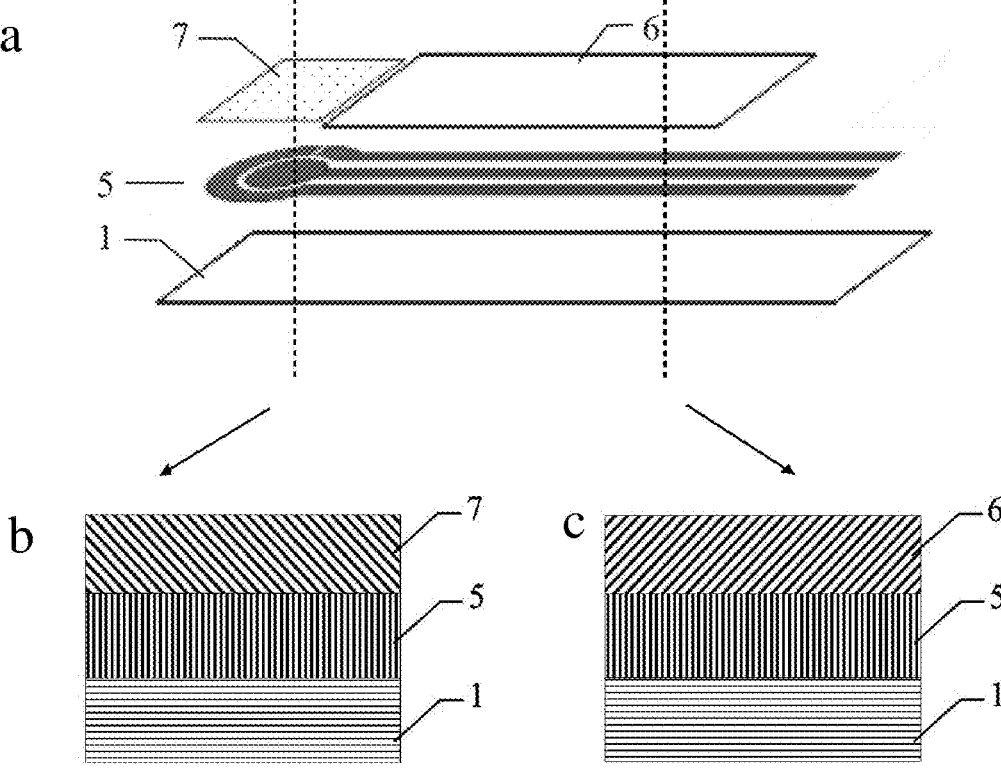
FIGS. 2A-2C are (a) an exploded view and (b-c) cross-sectional diagrams of the methane sensor of the present invention.

1. substrate; 2. working electrode; 3. reference electrode; 4. counter electrode; 5. conductive connection electrode; 6. insulating layer 7. sensing electrode.

DETAILED DESCRIPTION OF THE EMBODIMENTS

The following is a further description of the present invention in combination with an implementation example.

Example 1

A methane sensor, which is fabricated by the following steps. (1) preparation of substrate: cleaning the flexible PET substrate sheet and cutting it into uniform small pieces of 1 cm×5 cm as a flexible substrate 1.

(2) fabrication of the conductive connection electrode: printing or screen printing an electrode material on the substrate with a screen printer or a printer to form a conductive connection electrode 5, the conductive connection electrode 5 includes a working electrode 2, a reference electrode 3 and a counter electrode 4, using the conductive connection electrode 5 as a wire connecting the PEDOT:PSS sensing electrode 7 and the potentiostat, and further connected to a detection instrument or circuit board through the interface and then placing in an oven and drying at a temperature of 60° C. for 60 min.

(3) fabrication of the insulating layer: fabricating the insulating layer 6 on the conductive connection electrode 5 with a screen printer or a printer, exposing the sensing area connecting the external interface part and the PEDOT:PSS sensing electrode 7, then placing in the oven and drying at 60° C. for 60 min.

(4) fabrication of the sensing electrode: dropping the PEDOT:PSS solution at a concentration of 50% and a volume of 0.4 μL on the connection of the PEDOT:PSS sensing electrode 7 in the sensing area, putting in the oven, after drying, forming a film, that is, PEDOT:PSS sensing electrode 7, after taking out, placing in a refrigerator and storing at 4° C.

Example 2

A methane sensor, which is fabricated by the following steps. (1) preparation of substrate: cleaning the flexible PET substrate sheet, and then cutting into 1 cm×5 cm uniform pieces as a flexible substrate 1.

(2) fabrication of the conductive connection electrode: printing or screen printing an electrode material on the substrate with a screen printer or a printer to form a conductive connection electrode 5, the conductive connection electrode 5 includes a working electrode 2, a reference electrode 3 and a counter electrode 4, using the conductive connection electrode 5 as a wire to connect the PEDOT:PSS sensing electrode 7, and further connecting to the detection instrument or circuit board through the interface and then placing in an oven and drying at a temperature of 60° C. for 60 min.

(3) fabrication of the insulating layer: fabricating the insulating layer 6 on the conductive connection electrode 5 with a screen printer or a printer, exposing the sensing area connecting the external interface part and the PEDOT:PSS sensing electrode 7, then placing in the oven and drying at 60° C. for 60 min.

(4) fabrication of the sensing electrode: dropping PEDOT:PSS solution at a concentration of 50% and volume of 0.5 μL on the junction of PEDOT:PSS sensing electrode 7 in the sensing area, after drying in the oven, forming a film, that is, PEDOT:PSS sensing electrode 7, and then taking out and storing in a refrigerator at a temperature of 4° C.

Example 3

A methane sensor, which is fabricated by the following steps, (1) preparation of substrate: cleaning the flexible PET substrate sheet, and then cutting into 1 cm×5 cm uniform small pieces as a flexible substrate 1.

(2) fabrication of the conductive connection electrode: printing or screen printing an electrode material on the substrate with a screen printer or a printer to form a conductive connection electrode 5, the conductive connection electrode 5 includes a working electrode 2, a reference electrode 3 and a counter electrode 4, using the conductive connection electrode 5 as a wire connecting the PEDOT:PSS sensing electrode 7 and the potentiostat, and further connected to the detection instrument or circuit board through the interface and then placing in an oven and drying at a temperature of 60° C. for 60 min.

(3) fabrication of the insulating layer: fabricating the insulating layer 6 on the conductive connection electrode with a screen printer or a printer, and exposing the sensing area of the connecting external interface part and the PEDOT:PSS sensing electrode 7, then putting into the oven and drying at 60° C. for 60 min.

(4) fabrication of the sensing electrode: dropping the PEDOT:PSS solution at a concentration of 50% and a volume of 0.6 μL at the junction of the PEDOT:PSS sensing electrode 7 in the sensing area, after drying in the oven, forming a film, that is, the PEDOT:PSS sensing electrode 7, and then taking out and storing in a refrigerator at a temperature of 4° C.

Example 4

A methane sensor, which is fabricated by the following steps. (1) preparation of substrate: cleaning the flexible PET substrate sheet, and then cutting into 1 cm×5 cm uniform pieces as a flexible substrate 1.

(2) fabrication of the conductive connection electrode: printing or screen printing an electrode material on the substrate with a screen printer or a printer to form a conductive connection electrode 5, the conductive connection electrode 5 includes a working electrode 2, a reference electrode 3 and a counter electrode 4, using the conductive connection electrode 5 as a wire connecting the PEDOT:PSS sensing electrode 7 and the potentiostat, and further connecting to the detection instrument or circuit board through the interface and then placing in an oven and drying at a temperature of 60° C. for 60 min.

(3) fabrication of the insulating layer: fabricating the insulating layer 6 on the conductive connection electrode 5 with a screen printer or a printer, exposing the sensing area connecting the external interface part and the PEDOT:PSS sensing electrode 7, then placing in the oven and drying at 60° C. for 60 min.

(4) fabrication of the sensing electrode: dropping the PEDOT:PSS solution at a concentration of 50% and a volume of 0.7 μL at the junction of the PEDOT:PSS sensing electrode 7 in the sensing area, after drying in the oven, forming a film that is, the PEDOT:PSS sensing electrode 7, and then taking out and storing in a refrigerator at a temperature of 4° C.

Example 5

A methane sensor, which is fabricated by the following steps. (1) preparation of substrate: cleaning the flexible PET substrate sheet, and then cutting into 1 cm×5 cm uniform pieces as a flexible substrate 1.

(2) fabrication of the conductive connection electrode: printing or screen printing an electrode material on the substrate with a screen printer or a printer to form a conductive connection electrode 5, the conductive connection electrode 5 includes a working electrode 2, a reference electrode 3 and a counter electrode 4, using the conductive connection electrode 5 as a wire connecting the PEDOT:PSS sensing electrode 7 and the potentiostat, and further connecting to the detection instrument or circuit board through the interface and then placing in an oven and dried at a temperature of 60° C. for 60 min.

(3) fabrication of the insulating layer: fabricating the insulating layer 6 on the conductive connection electrode 5 with a screen printer or a printer, and exposing the sensing area connecting the external interface part and the PEDOT:PSS sensing electrode 7, then placing in the oven and drying at 60° C. for 60 min.

(4) fabrication of the sensing electrode: dropping the PEDOT:PSS solution at a concentration of 50% and a volume of 0.8 μL at the junction of the PEDOT:PSS sensing electrode 7 in the sensing area, after drying in the oven, forming a film, that is, the PEDOT:PSS sensing electrode 7, and then taking out and storing in the refrigerator at a temperature of 4° C.

Example 6

A methane sensor, which is fabricated by the following steps: (1) preparation of substrate: cleaning the flexible PET substrate sheet, and then cutting into 1 cm×5 cm uniform small pieces as a flexible substrate 1.

(2) fabrication of the conductive connection electrode: printing or screen printing an electrode material on the substrate with a screen printer or a printer to form a conductive connection electrode 5, the conductive connection electrode 5 includes a working electrode 2, a reference electrode 3 and a counter electrode 4, using the conductive connection electrode 5 as a wire connecting the PEDOT:PSS sensing electrode 7 and the potentiostat, and further connecting to the detection instrument or circuit board through the interface and then placing in an oven and drying at a temperature of 60° C. for 60 min.

(3) fabrication of the insulating layer: fabricating the insulating layer 6 on the conductive connection electrode 5 with a screen printer or a printer, exposing the sensing area connecting the external interface part and the PEDOT:PSS sensing electrode 7, then placing in the oven and drying at 60° C. for 60 min.

(4) fabrication of the sensing electrode: dropping the PEDOT:PSS solution at a concentration of 10% and a volume of 0.7 μL at the junction of the PEDOT:PSS sensing electrode 7 in the sensing area, after drying in the oven, forming a film, that is, the PEDOT:PSS sensing electrode 7, and then taking out and storing in a refrigerator at a temperature of 4° C.

Example 7

A methane sensor, which is fabricated by the following steps, (1) preparation of substrate: cleaning the flexible PET substrate sheet, and then cutting into uniform small pieces of 1 cm×5 cm as a flexible substrate 1.

(2) manufacturing conductive connection electrode: printing or screen printing an electrode material on the substrate with a screen printer or a printer to form a conductive connection electrode 5, the conductive connection electrode 5 includes a working electrode 2, a reference electrode 3, and a counter electrode 4, using the conductive connection electrode 5 as a wire to connect the PEDOT:PSS sensing electrode, and further connecting the detection instrument or circuit board through the interface and then putting into an oven and drying for 60 min at a temperature of 60° C.

(3) fabrication of the insulating layer: fabricating the insulating layer 6 on the conductive connection electrode 5 with a screen printer or a printer, exposing the sensing area connecting the external interface part and the PEDOT:PSS sensing electrode 7, then placing in the oven and drying at a temperature of 60° C. for 60 min.

(4) fabrication of the sensing electrode: dropping the PEDOT:PSS solution at a concentration of 20% and a volume of 0.7 L at the junction of the PEDOT:PSS sensing electrode 7 in the sensing area, after drying in the oven, forming a film, that is, the PEDOT:PSS sensing electrode 7, and then taking out and storing in the refrigerator at a temperature of 4° C.

Example 8

A methane sensor, which is fabricated by the following steps, (1) preparation of substrate: cleaning the flexible PET substrate, and then cutting into uniform small pieces of 1 cm×5 cm as a flexible substrate 1.

(2) fabrication of the conductive connection electrode: printing or screen printing an electrode material on the substrate with a screen printer or a printer to form a conductive connection electrode 5, the conductive connection electrode 5 includes a working electrode 2, a reference electrode 3 and a counter electrode 4, using the conductive connection electrode 5 as a wire to connect the PEDOT:PSS sensing electrode, and further connecting to the detection instrument or circuit board through the interface and then placing in an oven, drying at a temperature of 60° C. for 60 min.

(3) fabrication of the insulating layer: fabricating the insulating layer 6 on the conductive connection electrode 5 with a screen printer or a printer, and exposing the sensing area connecting the external interface part and the PEDOT:PSS sensing electrode 7, then placing in the oven and dried at a temperature of 60° C. for 60 min.

(4) fabrication of the sensing electrode: dropping the PEDOT:PSS solution at a concentration of 40% and a volume of 0.7 L at the junction of the PEDOT:PSS sensing electrode in the sensing area, after drying in the oven, forming a film, that is, the PEDOT:PSS sensing electrode, after taking out, placing in a refrigerator and storing at a temperature of 4° C.

Example 9

A methane sensor, which is fabricated by the following steps: (1) preparation of substrate: cleaning the flexible PET substrate sheet, and then cutting into 1 cm×5 cm uniform small pieces, as a flexible substrate 1.

(2) fabrication of the conductive connection electrode: printing or screen printing an electrode material on the substrate with a screen printer or a printer to form a conductive connection electrode 5, the conductive connection electrode 5 includes a working electrode 2, a reference electrode 3 and a counter electrode 4, using the conductive connection electrode 5 as a wire to connect the PEDOT:PSS sensing electrode, and further connecting to the detection instrument or circuit board through the interface and then placing in an oven, drying at a temperature of 60° C. for 60 min.

(3) fabrication of the insulating layer: fabricating the insulating layer 6 on the conductive connection electrode 5 with a screen printer or a printer, and exposing the sensing area of the connecting external interface part and the PEDOT:PSS sensing electrode 7, then placing in the oven and dried at a temperature of 60° C. for 60 min.

(4) fabrication of the sensing electrode: dropping PEDOT:PSS solution at a concentration of 60% and a volume of 0.7 μL at the junction of PEDOT:PSS sensing electrode 7 in the sensing area, after drying in the oven, forming a film, that is, PEDOT:PSS sensing electrode 7, after taking out, placing in a refrigerator and storing at a temperature of 4° C.

Example 10

A methane sensor, which is fabricated by the following steps, (1) preparation of substrate: cleaning the flexible PET substrate sheet, and then cutting into uniform small pieces of 1 cm×5 cm as a flexible substrate 1.

(2) manufacturing of the conductive connection electrode: printing or screen printing an electrode material on the substrate with a screen printer or a printer to form a conductive connection electrode 5, the conductive connection electrode 5 includes a working electrode 2, a reference electrode 3, and a counter electrode 4, using the conductive connection electrode 5 as a wire to connect the PEDOT:PSS sensing electrode, and further connecting the detection instrument or circuit board through the interface and then putting into an oven and drying for 60 min at a temperature of 60° C.

(3) fabrication of the insulating layer: fabricating the insulating layer 6 on the conductive connection electrode 5 with a screen printer or a printer, exposing the sensing area connecting the external interface part and the PEDOT:PSS sensing electrode 7, then placing in the oven and drying at a temperature of 60° C. for 60 min.

(4) fabrication of the sensing electrode: dropping the PEDOT:PSS solution at a concentration of 80% and a volume of 0.7 μL at the junction of the PEDOT:PSS sensing electrode 7 in the sensing area, after drying in the oven, forming a film, that is, the PEDOT:PSS sensing electrode 7, after taking out and storing in a refrigerator at a temperature of 4° C.

Example 11

A methane sensor, which is fabricated by the following steps, (1) preparation of substrate: cleaning the flexible PET substrate sheet, and then cutting into uniform small pieces of 1 cm×5 cm as a flexible substrate 1.

(2) manufacturing the conductive connection electrode: printing or screen printing an electrode material on the substrate with a screen printer or a printer to form a conductive connection electrode 5, the conductive connection electrode 5 includes a working electrode 2, a reference electrode 3 and a counter electrode 4, using the conductive connection electrode 5 as a wire to connect the PEDOT:PSS sensing electrode 5, and further connecting the detection instrument or circuit board through the interface and then putting into an oven, and dry for 60 min at a temperature of 60° C.

(3) fabrication of the insulating layer: fabricating the insulating layer 6 on the conductive connection electrode with a screen printer or a printer, and exposing the sensing area connecting the external interface part and the PEDOT:PSS sensing electrode 7, then placing in the oven and drying for 60 min at a temperature of 60° C.

(4) fabrication of the sensing electrode: dropping the PEDOT:PSS solution at a concentration of 100% and a volume of 0.7 L at the junction of the PEDOT:PSS sensing electrode 7 in the sensing area, after drying in the oven, forming a film, that is, the PEDOT:PSS sensing electrode, after taking out, placing in a refrigerator and storing at a temperature of 4° C.

Using a methane sensor made from examples 1-11 to detect methane.

Obtaining the pure methane gas from the gas cylinder, and preparing the methane mixed gas with a methane concentration of 20% by mixing pure methane and nitrogen, storing the methane mixed gas in a closed box, connecting the prepared methane sensor to a potentiostat and a computer with related software, the test adopts a potentiostatic mode and the voltage is set to 1 V, the connected methane sensor is quickly placed in a closed box containing a methane mixed gas to expose PEDOT:PSS to methane, and then testing the sensor for 5 seconds, and recording the changing current to detect the resistance of PEDOT.PSS, at the end of the test, taking the sensor out from the box and closing the box.

Analysis of the Test Results

Figure 3A:
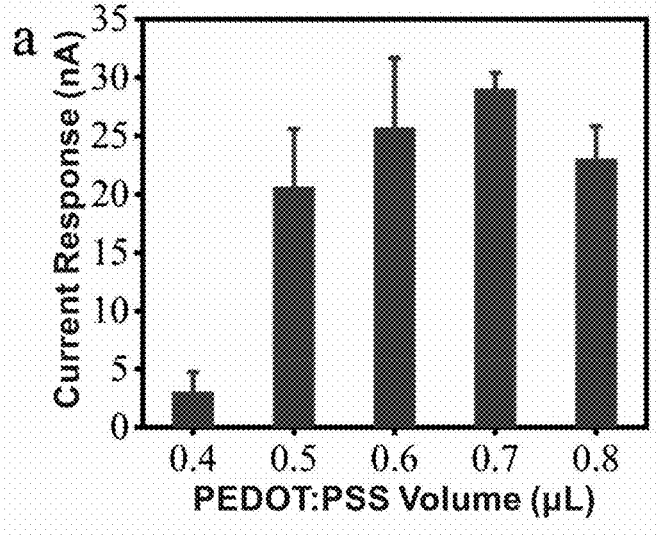
FIGS. 3A-3B are schematic diagrams of the current response of the methane sensor with different concentrations of PEDOT:PSS and different volumes of PEDOT:PSS of the present invention.
Figure 3B:
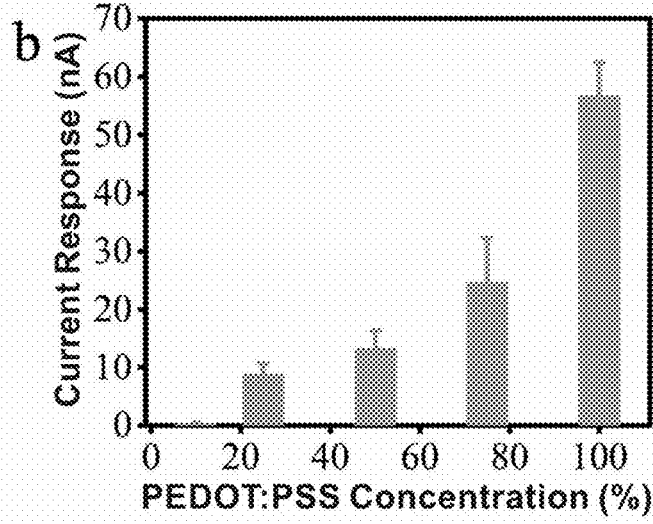

FIGS. 3A-3B show the current response diagrams of methane sensors with different concentrations of PEDOT:PSS and different volumes of PEDOT:PSS, wherein FIG. 3A is the current response diagram of the methane sensor made by examples 1-5, as shown in FIG. 3B, for detecting the methane gas in the closed box by the methane sensor of examples 1-5, as the volume of the PEDOT:PSS solution increased from 0.4 to 0.7 μL, the area and thickness of the PEDOT:PSS film gradually increased, and the current response also increased, that is, the sensitivity of the methane sensor gradually increased.

When the solution volume is 0.7 μL, the methane sensor shows the highest sensitivity, and the current response is 30 nA. When the solution volume reaches 0.8 μL, the current response is lower than that when the solution volume is 0.7 μL. This is due to the effect of surface tension and the nature of the liquid itself. When the volume of the solution is 0.8 μL, the area of the PEDOT:PSS film is limited compared with that when the volume of the solution is 0.7 μL. Therefore, the sensitivity when the volume of the solution is 0.8 μL is less than that when the volume of the solution is 0.7 μL.

FIG. 3B is the current response diagram of the methane sensor made by examples 6-11, the volume of PEDOT:PSS solution is 0.7 μL, with the increase of the concentration of PEDOT:PSS solution, the current response is also greater, when the concentration is 100%, the methane sensor shows the highest sensitivity, and the current response is 50 nA.

The results show that the PEDOT:PSS methane sensor has the best sensitivity when the concentration of PEDOT:PSS solution is 100% and the volume is 0.7 μL. The thicker the PEDOT:PSS film is, the more methane molecules are captured, and the higher the sensitivity is.

Figure 4A:
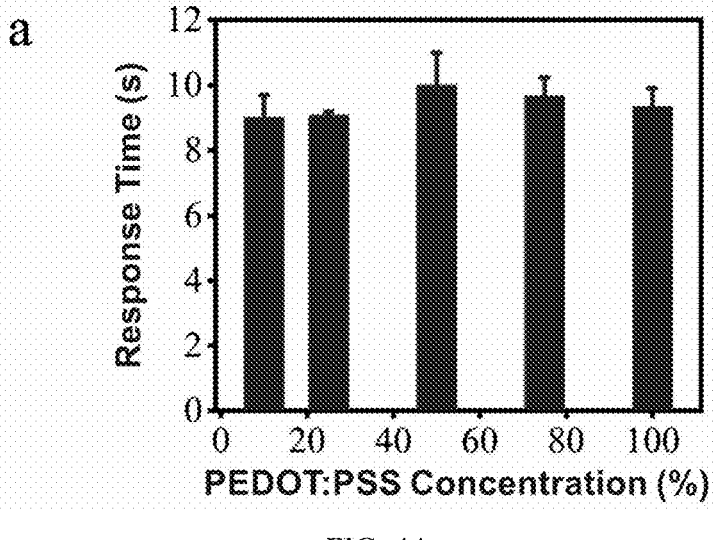
FIGS. 4A-4B are schematic diagrams of the response time of the methane sensor with different concentrations of PEDOT:PSS and different volumes of PEDOT:PSS of the present invention.
Figure 4B:
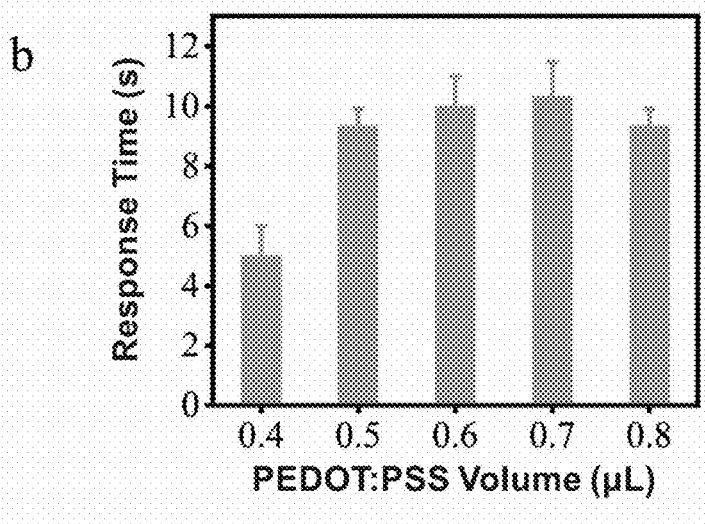

FIGS. 4A-4B are schematic diagrams of the response time of the methane sensor with different concentrations of PEDOT:PSS and different volumes of PEDOT:PSS, FIG. 4A is a schematic diagram of the response time of the methane sensor with the examples 1-5. As shown in FIGS. 4A-4B, the response time of the methane sensor is not much different, that is, the concentration of the PEDOT:PSS solution has little effect on the response time. FIG. 4B is the response time diagram of the methane sensor of the examples 6-11. As shown in FIGS. 4A-4B, when the volume of PEDOT:PSS solution changes from 0.4 μL to 0.5 μL, the response time changes greatly, and the response time changes little between 0.5-0.8 μL. Therefore, when the volume of PEDOT:PSS solution is small, it will affect the response time. When the volume of PEDOT:PSS solution is large, it has little effect on the response time.

The methane sensor is taken out of the closed box and placed in the ambient air or nitrogen environment. The methane sensor is not capturing methane, so that no electrons are generated, and the resistance of the methane sensor is restored.

Figure 5A:
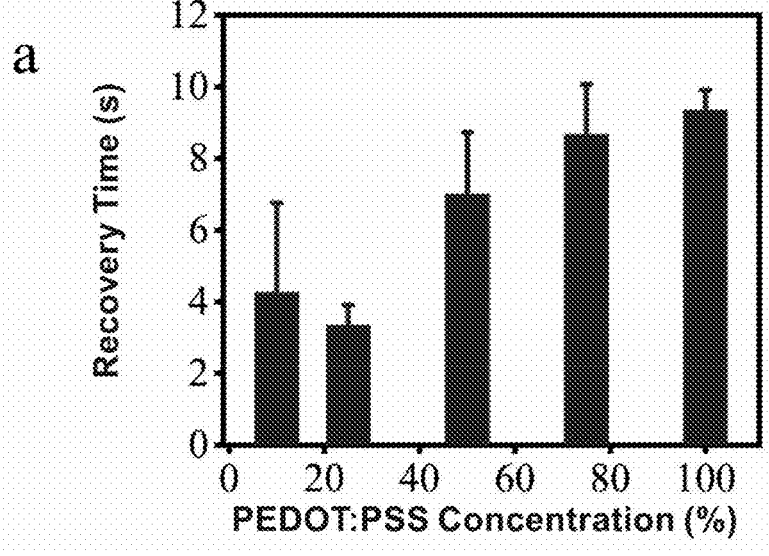
FIGS. 5A-5B are schematic diagrams of the recovery time of the methane sensor with different concentrations of PEDOT:PSS and different volumes of PEDOT:PSS of the present invention.
Figure 5B:
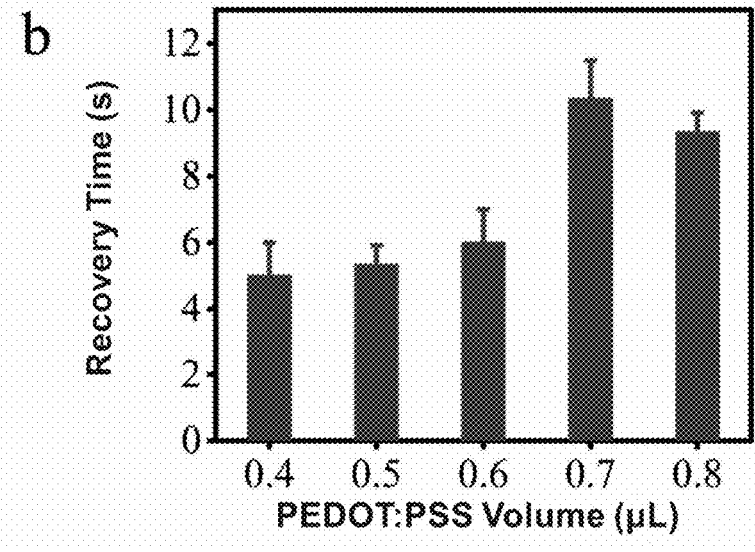

FIGS. 5A-5B are schematic diagrams of the recovery time of the methane sensor with different concentrations of PEDOT:PSS and different volumes of PEDOT:PSS. FIG. 5A is a schematic diagram of the recovery time of the methane sensor with the examples 1-5, as shown in FIGS. 5A-5B, the recovery time increases with the increase of the concentration. FIG. 5B is a schematic diagram of the recovery time of the methane sensor with the examples 6-11, as shown in FIGS. 5A-5B, the recovery time increases gradually with the increase of the volume, and the recovery time when the solution volume is 0.8 μL is slightly less than the recovery time when the solution volume is 0.7 μL.

It can be seen that the thicker the PEDOT:PSS film is, the longer the recovery time is. The thicker the film is, the deeper the methane molecules enter the film, and the more methane molecules are captured, so that the methane molecules are separated from the PEDOT:PSS film, the longer the time is required.

The methane sensor prepared by example 11 is selected to study its ability to detect methane, placing the sensor in a box containing different concentrations of methane from $2 \times 10^5$ ppm to $1 \times 10^6$ ppm, and recording the current-time curve by an electrochemical workstation.

Figures 6, 7:
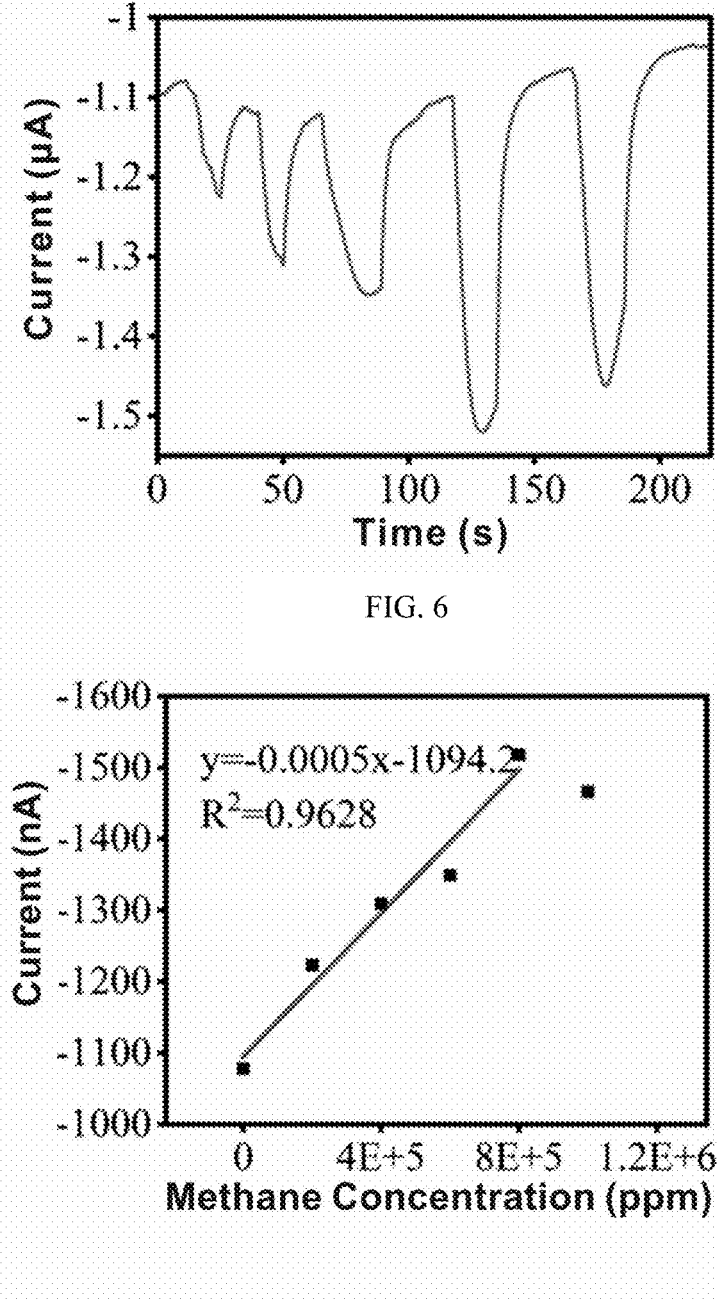
FIG. 6 is a schematic diagram of the current curve of the methane sensor in different concentrations of methane of the present invention.
FIG. 7 is a schematic diagram of the calibration curve drawn by the methane sensor of the invention in different concentrations of methane of the present invention.

FIG. 6 shows the current curve of the methane sensor in different concentrations of methane, the methane sensor shows a fast response time of 12 seconds and a recovery time of 5 seconds.

FIG. 7 shows the calibration curves of the methane sensor in different concentrations of methane, as shown in FIG. 7, the methane sensor shows a high sensitivity of 0.5 pA/ppm and a wide detection range from 0 to $0.8 \times 10^6$ ppm. The detection limit is calculated to be 600 ppm, which is much higher than the minimum explosion concentration of methane. Therefore, the methane sensor prepared by the invention has high sensitivity.

The flexibility of the device is crucial for integration into applications. In order to analyze the flexibility of the PEDOT:PSS methane sensor, a bending test was performed. Testing the methane sensor for changes in the resistance and relative resistivity of the bent detector at different bending times and different bending angles.

Figures 8A, 8B:
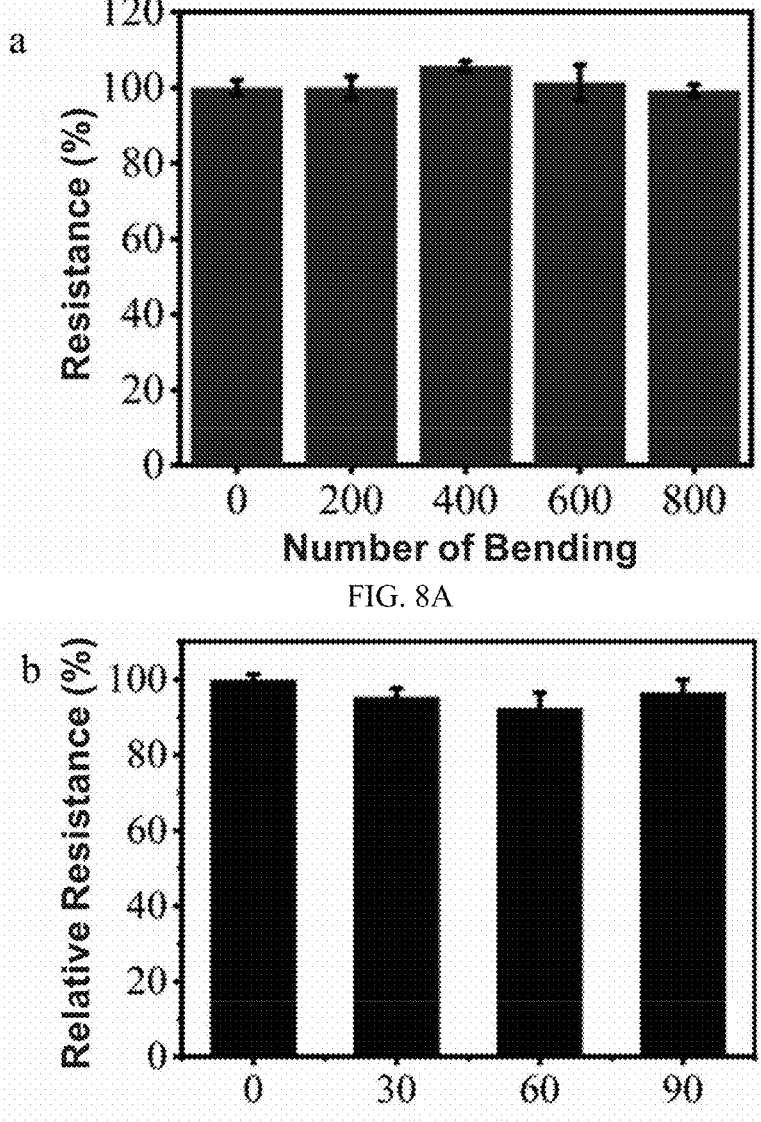
FIGS. 8A-8B are flexibility diagrams of the methane sensor of the present invention.

FIGS. 8A-8B are schematic diagrams of the flexibility of the methane sensor, where FIG. 8A is a schematic diagram of the resistance of the methane sensor under different bending times. As shown in FIGS. 8A-8B, the sensor still maintains a high degree of stability after multiple bending. FIG. 8B is a schematic diagram of the relative resistivity of the methane sensor at different bending degrees. As shown in FIGS. 8A-8B, when bending from 30 degrees to 90 degrees, its resistance does not change significantly, which proves that the sensor has good flexibility and can be easily integrated.

Figures 9, 10:
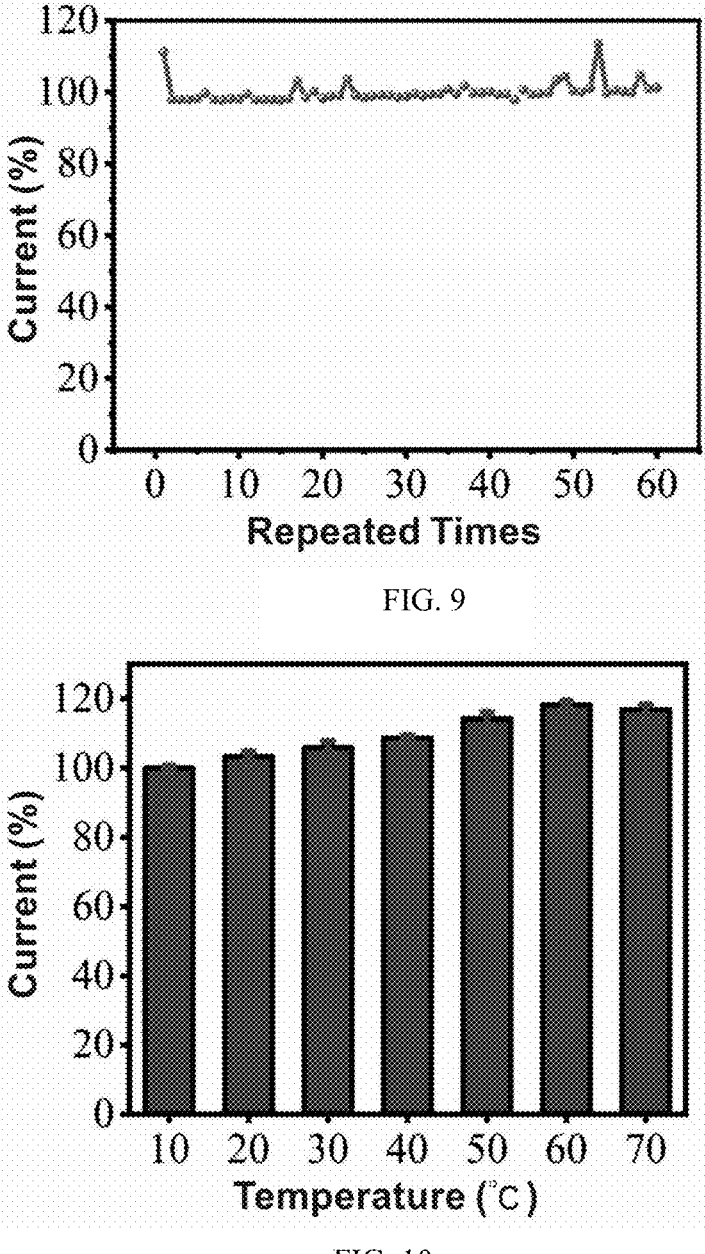
FIG. 9 is a repeatability experiment diagram of the methane sensor of the present invention.
FIG. 10 is a schematic diagram of the effect of temperature on the methane sensor of the present invention.

FIG. 9 is a schematic diagram of the repeatability experiment of the methane sensor of the invention. As shown in FIG. 9, in order to evaluate the repeatability of the sensor, a sensor has continuously tested methane for 60 times, and the results show good repeatability.

FIG. 10 shows the effect of temperature on the methane sensor. As shown in FIG. 10, when the temperature reaches 70° C., the resistance decreases by about 14%.

Figures 11, 12:
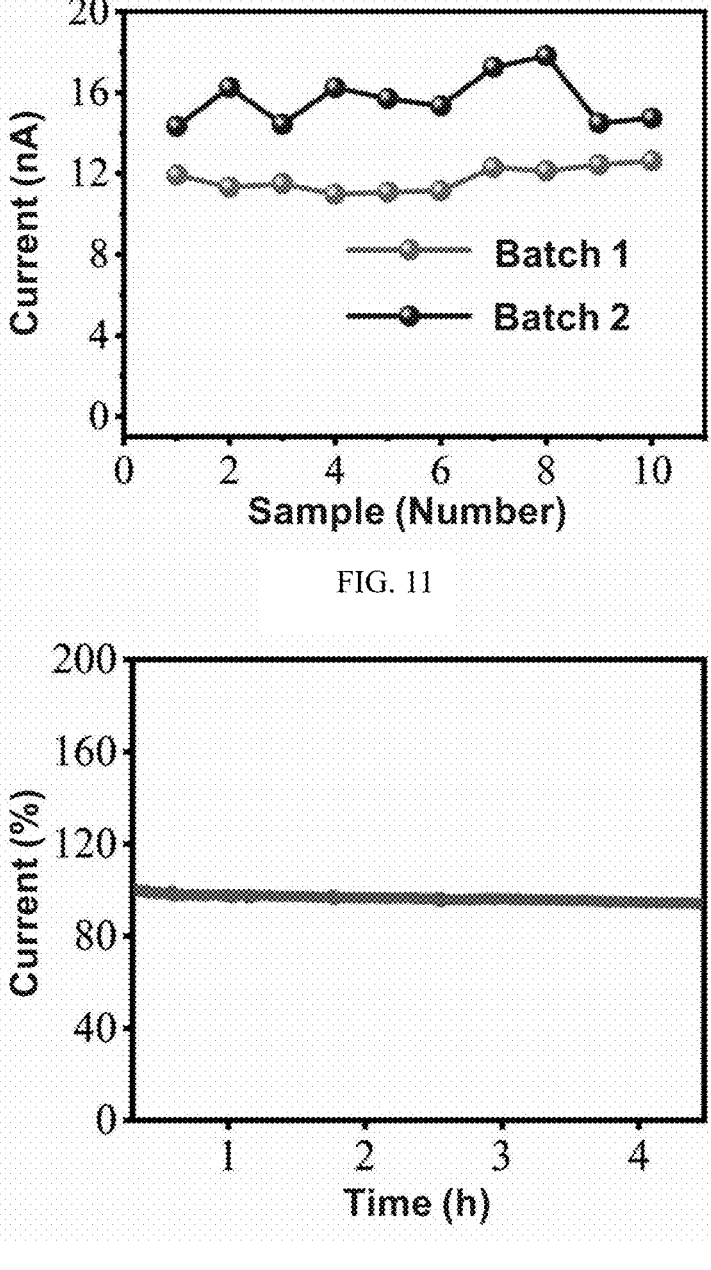
FIG. 11 is a current error diagram of methane sensors prepared in different batches of the present invention.
FIG. 12 is a schematic diagram of the current signal of a single sensor for detecting a constant concentration of methane of the present invention.

FIG. 11 is a schematic diagram of the current error of the methane sensor prepared in different batches. As shown in FIG. 11, FIG. 11 shows that the error of the sensor prepared in different batches is 16%. These may be caused by several factors, such as the inhomogeneity of screen printing, the error of manual dripping of PEDOT:PSS, the temperature and humidity during the preparation process, etc. Errors in the same batch may be caused by errors in the electrochemical workstation, inhomogeneity of screen printing, effects of temperature and humidity, position of the sensor in the methane container, and poor contact between the sensor and the instrument. These errors can be solved by strictly controlling the preparation conditions and industrialization processes.

FIG. 12 is a schematic diagram of the current signal of a single sensor for detecting a constant concentration of methane. As shown in FIG. 12, the current does not change significantly within 4 hours (4%), indicating that the sensor has good stability.

Figure 13:
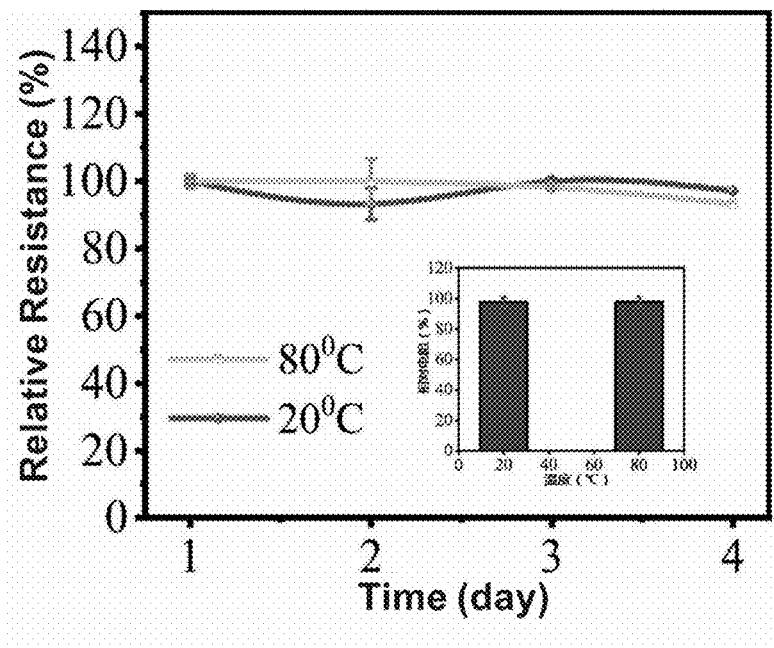
FIG. 13 is a schematic diagram of the aging effect of the methane sensor of the present invention.

To verify the aging effect of the sensor, FIG. 13 is a schematic diagram of the aging effect of the methane sensor of the invention. As shown in FIG. 13, the relative resistance change of the sensor is less than 7% after 4 days of storage at 20° C. and 80° C., indicating that the aging effect of a few days is very small when the temperature is lower than 80° C.

In summary, a methane sensor of the invention has the characteristics of high flexibility, low cost, fast response, and high sensitivity.

Finally, it should be explained that the above examples are only used to explain the technical scheme of the invention rather than restrict it. Although the invention is described in detail with reference to the better embodiment, the ordinary technical personnel in this field should understand that they can still modify or replace the technical scheme of the invention, and these modifications or equivalent substitutions cannot make the modified technical scheme out of the spirit and scope of the technical scheme of the present invention.

What is claimed is:

1. A methane sensor, comprising
   a substrate, a conductive connection electrode, and a sensing electrode, wherein the conductive connection electrode is arranged on the substrate;
   the conductive connection electrode is an electrochemical electrode, including two electrodes or three electrodes, when there are two electrodes, it is a working electrode and a counter electrode, when there are three electrodes, it is a working electrode, a reference electrode and a counter electrode;

the conductive connection electrode serves as a wire that is connected to a detection instrument or a circuit board through an interface, and is connected to the sensing electrode;
   the sensing electrode is covered on the conductive connection electrode, the sensing electrode is a layer of a conductive polymer film, and the conductive connection electrode is coated with an insulating layer in addition to a sensing area; and the sensing electrode is configured to capture methane molecules, so that a current response of the methane sensor changes due to change of a resistance of the sensing electrode caused by the presence of methane;
   the conductive polymer is poly (3,4-ethylenedioxythiophene): poly (styrene sulfonic acid) (PEDOT:PSS), and the conductive polymer is made into the conductive polymer film by a screen printing method, a printing method, or a coating method; and
   the conductive connection electrode connects with the sensing electrode.

2. The methane sensor according to claim 1, wherein the conductive connection electrode is made of one material of a gold composite paste, a platinum composite paste, or a carbon composite paste, and is manufactured by screen printing or another printing method.

3. The methane sensor according to claim 1, wherein a material of the substrate is either a flexible material that is at least one of polyethylene terephthalate, polyimide, polyvinyl chloride, acrylonitrile butadiene, and styrene, or a material of the substrate is one of the following hard materials silicon, glass, and ceramics.

4. A preparation method of the methane sensor according to claim 1 comprising the following steps:
   (1) preparing a substrate by washing a substrate sheet clean, and then cutting the sheet into 1 cm×5 cm uniform small pieces as substrates;
   (2) fabricating the conductive connection electrode by printing or screen printing an electrode material on one of the substrates with a screen printer or a printer to form the conductive connection electrode, and then putting the substrate into an oven for drying of the conductive connection electrode;
   (3) making an insulating layer on the conductive connection electrode by using a screen printer or a printer to expose a sensing area, and then putting the substrate into an oven for drying of the insulating layer;
   (4) fabricating the sensing electrode by dropping a conductive polymer solution in the sensing area, and then putting the substrate into an oven for drying to form a film that is the sensing electrode, wherein a concentration of the conductive polymer solution is 100% PEDOT:PSS and a volume is 0.7 μL.

5. The preparation method of the methane sensor according to claim 4, wherein in the step (2) an oven drying temperature range is 30-100° C., and a drying time is 5-100 min; and in the step (3) an oven drying temperature range is 30-100° C., and a drying time is 5-100 min.

* * * * *